United States Patent
Hummel et al.

(10) Patent No.: US 7,504,642 B2
(45) Date of Patent: Mar. 17, 2009

(54) PHOTOLUMINESCENCE IMAGING WITH PREFERENTIAL DETECTION OF PHOTOLUMINESCENCE SIGNALS EMITTED FROM A SPECIFIED MATERIAL LAYER OF A WAFER OR OTHER WORKPIECE

(75) Inventors: Steven G. Hummel, Bend, OR (US); Tom Walker, Portland, OR (US)

(73) Assignee: Nanometrics Incorporated, Milpitas, CA (US)

( * ) Notice: Subject to any disclaimer, the term of this patent is extended or adjusted under 35 U.S.C. 154(b) by 92 days.

(21) Appl. No.: 11/426,877

(22) Filed: Jun. 27, 2006

(65) Prior Publication Data

US 2007/0008518 A1    Jan. 11, 2007

Related U.S. Application Data

(60) Provisional application No. 60/696,853, filed on Jul. 6, 2005.

(51) Int. Cl.
  *G01N 21/64* (2006.01)
(52) U.S. Cl. .................................. 250/458.1; 250/400
(58) Field of Classification Search ................ 250/400, 250/458.1; 356/237.1
  See application file for complete search history.

(56) References Cited

U.S. PATENT DOCUMENTS

| | | | |
|---|---|---|---|
| 3,841,927 A | 10/1974 | Florence et al. | |
| 3,998,669 A | 12/1976 | Florence et al. | |
| 4,246,793 A | 1/1981 | Fairand et al. | |
| 4,511,800 A | 4/1985 | Harbeke et al. | |
| 4,740,694 A | 4/1988 | Nishimura et al. | |
| 4,978,862 A | 12/1990 | Silva et al. | |
| 5,202,744 A | 4/1993 | Louis | |
| 5,244,820 A | 9/1993 | Kamata et al. | |
| 5,539,514 A | 7/1996 | Shishido et al. | |

(Continued)

FOREIGN PATENT DOCUMENTS

JP    11-274257    10/1999

(Continued)

OTHER PUBLICATIONS

Bajaj, J. et al. (Jun. 1, 1993). "Spatially resolved characterization of HGCDTE materials and devices by scanning laser microscopy," *Semiconductor Science and Technology* 8(6S):872-877.

(Continued)

*Primary Examiner*—Constantine Hannaher
*Assistant Examiner*—Djura Malevic
(74) *Attorney, Agent, or Firm*—Silicon Valley Patent Group LLP (57) ABSTRACT

A method and apparatus uses photoluminescence to identify defects in one or more specified material layers of a sample. One or more filtering elements are used to filter out predetermined wavelengths of return light emitted from a sample. The predetermined wavelengths are selected such that only return light emitted from one or more specified material layers of the sample is detected. Additionally or alternatively, the wavelength of incident light directed into the sample may be selected to penetrate the sample to a given depth, or to excite only one or more selected material layers in the sample. Accordingly, defect data characteristic of primarily only the one or more specified material layers is generated.

19 Claims, 3 Drawing Sheets

U.S. PATENT DOCUMENTS

| | | | |
|---|---|---|---|
| 5,659,187 | A * | 8/1997 | Legoues et al. ............. 257/190 |
| 5,995,217 | A | 11/1999 | Watanabe |
| 6,075,592 | A | 6/2000 | Banerjee et al. |
| 6,108,079 | A | 8/2000 | Maeshima et al. |
| 6,160,615 | A | 12/2000 | Matsui et al. |
| 6,214,560 | B1 | 4/2001 | Yguerabide et al. |
| 6,251,754 | B1 | 6/2001 | Oshima et al. |
| 6,256,092 | B1 | 7/2001 | Tomita et al. |
| 6,429,968 | B1 | 8/2002 | Carver |
| 6,462,817 | B1 * | 10/2002 | Strocchia-Rivera ......... 356/369 |
| 6,628,111 | B2 | 9/2003 | Shapiro et al. |
| 6,893,936 | B1 * | 5/2005 | Chen et al. .................. 438/407 |
| 6,911,347 | B2 | 6/2005 | Higgs |
| 7,113,276 | B1 | 9/2006 | Higgs et al. |
| 7,139,083 | B2 * | 11/2006 | Fielden et al. .............. 356/630 |
| 7,140,202 | B2 | 11/2006 | Freund et al. |
| 7,245,696 | B2 | 7/2007 | Yun et al. |
| 7,306,951 | B1 | 12/2007 | Benson et al. |
| 2002/0054295 | A1 | 5/2002 | Maris |
| 2002/0088952 | A1 | 7/2002 | Rao et al. |
| 2002/0119485 | A1 | 8/2002 | Morgan |
| 2003/0061212 | A1 | 3/2003 | Smith et al. |
| 2003/0094579 | A1 * | 5/2003 | Hasegawa et al. ........ 250/458.1 |
| 2004/0092042 | A1 | 5/2004 | Higgs |
| 2004/0252297 | A1 | 12/2004 | Fairley et al. |
| 2006/0262296 | A1 | 11/2006 | Higgs |
| 2006/0281281 | A1 | 12/2006 | Tanzawa et al. |
| 2007/0000434 | A1 | 1/2007 | Buczkowski |
| 2007/0007466 | A1 | 1/2007 | Laurent et al. |
| 2007/0008526 | A1 | 1/2007 | Buczkowski |
| 2007/0176119 | A1 | 8/2007 | Hummel |

FOREIGN PATENT DOCUMENTS

| | | |
|---|---|---|
| JP | 11-354599 | 12/1999 |
| JP | 2000-193597 A | 7/2000 |
| JP | 2003-045928 A | 2/2003 |
| WO | WO-98/11425 A1 | 3/1998 |
| WO | WO-02/29883 A1 | 4/2002 |
| WO | WO-02/077621 A1 | 10/2002 |
| WO | WO-2004/010121 A1 | 1/2004 |
| WO | WO-2004-090516 A1 | 10/2004 |
| WO | WO-2007/005438 A2 | 1/2007 |
| WO | WO-2007/005438 A3 | 1/2007 |
| WO | WO-2007/008311 A2 | 1/2007 |
| WO | WO-2007/008399 A2 | 1/2007 |
| WO | WO-2007/008399 A3 | 1/2007 |
| WO | WO-2007/008430 A2 | 1/2007 |
| WO | WO-2007/008430 A3 | 1/2007 |

OTHER PUBLICATIONS

Bellone, S. et al. (1991). "Recombination measurement of n-type heavily doped layer in high-low silicon junctions," *IEEE Trans. Electron. Devices* 38(3):532-537.

Commerce, B. et al. (Sep. 1998). "Control of the fabrication steps of InP MIS transistors by means of scanning photoluminescence measurements," *Journal de Physique*, Colloque, Paris, France 49(C-4)(Suppl. 9): 431-436.

Derbyshire, K. (Summer 2004). "The engineered substrate's balancing act: performance gains versus greater costs and increased yield risks," *Yield Management Solutions Magazine* located at http://www.kla-tencor.com/company/magazine/summer04/coverstory.pdf, pp. 29.

DiStefano, T.H. et al. (Feb. 1987). "Non-destructive, non-contacting test of Si wafers by thermore-flectance," *IBM Technical Disclosure Bulletin*, 10 pages.

Fitzgerald, E.A. et al. (Nov. 3, 1998). "Dislocations in relaxed SiGe/Si heterostructures," MIT Department of Materials Science and Engineering and AmberWave Technologies, pp. 227-238.

Higgs, V et al. (Feb. 15, 1993). "Characterization of compositionally graed Si1-xGex alloy layers by photoluminescence spectroscopy and by cathodoluminescence spectroscopy and imaging," *Journal of Applied Physics* 73(4):152-156.

Higgs, V. (2000). Characterization of Si, SiGe, and SOI structures using photoluminescence, *Materials Research Society Symposium Proceedings* 588:129-140.

Higgs, V. et al. (Sep. 13, 1999). "Application of room temperature photoluminescence for the characterization of impurities and defects in silicon," *Proceedings of SPIE* 3895:21-37.

Korsunska, N.E. et al. (Jul. 2004). "High temperature photoluminescence spectroscopy in p-type SiC," *Semiconductor Science and Technology* 19(7):833-838.

Miner, C.J. (1992). "Non-destructive, whole wafer assessment of optoelectronic epitaxial materials," *Semicond. Sci. Technol.* 7:A10-A15.

Montangero, P. et al. (May 1, 1994). "Optical-beam-induced current and photoluminescence techniques for localization of crystallographic defects in optoelectronic devices," *Materials Science and Engineering B* B24(1/03):175-179.

Moore, C.J.L. et al. (Jun. 1990). "A spatially resolved spectrally resolved photoluminescence mapping system," *J. Crystal Growth* 103(1/4):21-27.

Pritchard, R.E. et al. (Jun. 1, 1993). "Composition assessment by spatially resolved photoluminescence of INGAAS and INGAASP epilayers grown on recessed INP substrates," *Semiconductor Science and Technology* 8(6):1166-1172.

Ressel, P. et al. (1993). "Optimized proton implantation step for vertical-cavity surface-emitting lasers," *Electron. Lett.* 29(10):918-919.

Ribes, A.C. et al. (May 1, 1995). "Photoluminescence imaging of porous silicon using a confocal scanning laser macroscope/microscope," *Applied Physics Letters* 66(18):2321-2323.

Tajima, M. (1990). "Characterization of semiconductors by photoluminescence mapping at room temperature," *Journal of Crystal Growth* 130:1-7.

Tajima, M. et al. (1990). "Mapping of microdefects in silicon crystals by photoluminescence at room temperature," *Semiconductor Silicon 1990* from *Proceedings of the Sixth International Symposium on Silicon Materials Science and Technology*, eds. H. R. Huff et al., Electrochem. Soc., Inc.: Pennington, NJ, pp. 994-1004.

Titus, J. (Jun. 1, 2004). "Keep an eye on wafer defects," *Test & Measurement World* located at http://www.reed-electronics.com/tmworld/article/CA420488.html, 5 pages.

Westrate, S. et al. (Feb. 2002). "Photoluminescence mapping detects CU contamination in SI wafers," *Solid State Technology* 45(2):57-58.

"RPM2000 Rapid Photoluminescence Mapper," Sales Brochure, Date Unknown, 6 pages.

"SPHER: The key to revealing hidden problems in Siwafers," Sales Brochure, Date Unknown, 8 pages.

Office Action mailed on Jan. 5, 2000 for U.S. Appl. No. 09/254,521, filed Mar. 8, 1999 by Higgs et al., 6 pages.

Response to Office Action mailed on Sep. 19, 2005 for U.S. Appl. No. 09/254,521, filed Mar. 8, 1999 by Higgs et al., 14 pages.

Notice of Allowance mailed on May 18, 2006 for U.S. Appl. No. 09/254,521, filed Mar. 8, 1999 by Higgs et al., 14 pages.

Restriction Requirement mailed on Jun. 14, 2007 for U.S. Appl. No. 11/177,735, filed Jul. 8, 2005 by Buczkowski, 6 pages.

Response to Restriction Requirement mailed on Jul. 23, 2007 for U.S. Appl. No. 11/177,735, filed Jul. 8, 2005 by Buczkowski, 16 pages.

Office Action mailed on Sep. 12, 2007 for U.S. Appl. No. 11/177,735, filed Jul. 8, 2005 by Buczkowski, 42 pages.

Ex Parte Quayle Action mailed on Jun. 11, 2007 for U.S. Appl. No. 11/427,080, filed Jun. 28, 2006 by Laurent et al., 6 pages.

Request for Continued Examination and Amendment mailed on Aug. 10, 2007 for U.S. Appl. No. 11/427,080, filed Jun. 28, 2005 by Laurent et al., 5 pages.

Office Action mailed on Oct. 10, 2007 for U.S. Appl. No. 11/427,080, filed Jun. 28, 2006 by Laurent et al., 7 pages.

International Search Report mailed on Dec. 18, 1997 for PCT Application No. PCT/GB97/02388 filed on Sep. 5, 1997 by Bio-Rad Micromeasurements, Ltd, 2 pages.

International Search Report mailed on Aug. 31, 2007 for PCT Application No. PCT/US06/25083 filed on Jun. 27, 2006 by Accent Optical Technologies, Inc., 4 pages.

International Search Report mailed on Oct. 1, 2007 for PCT Application No. PCT/US06/24938 filed on Jun. 27, 2006 by Accent Optical Technologies, Inc., 4 pages.

International Search Report mailed on Sep. 4, 2007 for PCT Application No. PCT/US06/25257 filed on Jun. 28, 2006 by Nanometrics, Inc., 2 pages.

International Search Report mailed on Jul. 22, 2004 for PCT Application No. PCT/GB2004/001521 filed on Apr. 8, 2004 by AOTI Operating Inc., 4 pages.

Office Action mailed on Dec. 11, 2007, for U.S. Appl. No. 11/528,723, filed Sep. 26, 2006 by Higgs, 7 pgs.

Response to Office Action mailed Jan. 30, 2008, for U.S. Appl. No. 11/528,723, filed Sep. 26, 2006, by Higgs, 15 pgs.

Ivanov, I.G. et al., "Donor doping calibration in 4H-SiC using photoluminescence spectroscopy", IEEE 1996, 0-7803-3179-Jun. 1996, pp. 223-226.

Response to Office Action with RCE and Amendment filed Jan. 30, 2008 for U.S. Appl. No. 11/528,723 filed on Sep. 26, 2006 by Higgs et al. 15 pages.

Notice of Allowance mailed by Examiner Michelle R. Connelly Cushwa on May 1, 2008 for U.S. Appl. No. 11/528,723 filed on Sep. 26, 2006 by Higgs et al., 7 pages.

RCE and IDS mailed Jul. 24, 2008 for U.S. Appl. No. 11/528,723 filed on Sep. 26, 2006 by Higgs et al., 4 pages.

Notice of Allowance mailed by Examiner Michelle R. Connelly Cushwa on Aug. 18, 2008 by Examiner Michelle R. Cushwa Connelly for U.S. Appl. No. 11/528,723 filed Sep. 26, 2006 by Higgs et al., 7 pages.

RCE and IDS mailed on Aug. 27, 2008 for U.S. Appl. No. 11/528,723 filed on Sep. 26, 2006 by Higgs et al., 5 pages.

Response to Office Action mailed on Feb. 12, 2008 for U.S. Appl. No. 11/177,735 filed on Jul. 8, 2005 by Buczkowski, 22 pages.

Office Action mailed by Examiner Rebecca Slomski on Jun. 23, 2008 for U.S. Appl. No. 11/177,735 filed on Jul. 8, 2005 by Buczkowski, 33 pages.

Office Action mailed by Examiner David S. Baker on Jun. 2, 2008 for U.S. Appl. No. 11/343,500 filed on Jan. 30, 2006 by Hummel et al., 32 pages.

Response to Office Action mailed on Mar. 27, 2008 for U.S. Appl. No. 11/427,080 filed on Jun. 28, 2006 by Laurent et al., 6 pages.

Notice of Allowance mailed by Examiner Mindy D. Vu on Jun. 5, 2008 by Examiner Mindy D. Vu for U.S. Appl. No. 11/427,080 filed on Jun. 28, 2006 by Laurent et al., 10 pgs.

Request for Continued Examination and IDS mailed on Aug. 28, 2008 for U.S. Appl. No. 11/427,080 filed on Jun. 28, 2006 by Laurent et al., 5 pages.

Office Action mailed by Examiner Isiako O. Akanbi on May 27, 2008, for U.S. Appl. No. 10/549,865, filed on Jul. 28, 2006 by Higgs, 19 pgs.

Response to Office Action dated Aug. 27, 2008 for U.S. Appl. No. 10/549,865, filed on Jul. 28, 2006 by Higgs, 10 pgs.

Notice of Allowance mailed by Examiner Mindy D. Vu on Sep. 12, 2008 by Examiner Mindy D. Vu for U.S. Appl. No. 11/427,080 filed on Jun. 28, 2006 by Laurent et al., 9 pgs.

Final rejection Office Action mailed by Examiner Isiako O. Akanbi on Dec. 3, 2008, for U.S. Appl. No. 10/549,865, filed on Jul. 28, 2006 by Higgs, 17 pgs.

* cited by examiner

PHOTOLUMINESCENCE IMAGING WITH PREFERENTIAL DETECTION OF PHOTOLUMINESCENCE SIGNALS EMITTED FROM A SPECIFIED MATERIAL LAYER OF A WAFER OR OTHER WORKPIECE

PRIORITY CLAIM

This application claims the benefit of U.S. Provisional Application No. 60/696,853, filed Jul. 6, 2005, which is incorporated herein by reference.

BACKGROUND

Photoluminescence imaging or photoluminescence spectroscopy is a contactless, nondestructive method of probing the electronic structure of materials, such as silicon semiconductor wafers, as well as other workpieces and materials. In a typical photoluminescence process, light is directed onto a wafer or other workpiece or sample (hereinafter collectively referred to as a "wafer"), where at least some of the light is absorbed. The absorbed light imparts excess energy into the material via a process of "photo-excitation." This excess energy is dissipated by the wafer through a series of pathways; one such pathway is the emission of light, or photoluminescence. The intensity and spectral content of this photoluminescence is directly related to various material properties of the wafer.

Photoluminescence imaging processes may be used to identify and quantify defects and contaminants present in the wafer based on spatial variations in the photoluminescence images produced. One photoluminescence imaging process, as described in International Application Number PCT/GB97/02388 (publication number WO 98/11425), which is incorporated herein by reference, involves probing the surface and/or the sub-surface bulk region of the wafer with one or more lasers of varying excitation wavelengths. A laser of a given wavelength is directed into the wafer and penetrates the wafer to a given depth. Return light emitted from excited regions of the wafer is detected and quantified by a detection system. Images of the measured return light, including spatial images of defects and contaminants in the wafer, may then be produced by the detection system or by an associated image-producing system.

While these photoluminescent images may effectively identify defects and contaminants in the wafer as a whole, it is sometimes difficult to readily identify the location and concentration of defects in a specific material layer of the wafer. For example, if two or more material layers of the wafer are penetrated by a laser, images of defects in the second material layer may obscure images of defects in the first material layer. This can be problematic if detailed defect data about only the first material layer is desired. Thus, there is a need to be able to obtain more accurate measurements of the location and concentration of defects in a specific material layer or layers of a wafer.

SUMMARY

A method and apparatus uses photoluminescence to identify defects in one or more specified material layers of a sample. One or more filtering elements are used to filter out predetermined wavelengths of return light emitted from a sample. The predetermined wavelengths are selected such that only return light emitted from one or more specified material layers of the sample is detected. Additionally or alternatively, the wavelength of incident light directed into the sample may be selected to penetrate the sample to a given depth, or to excite only one or more selected material layers in the sample. Accordingly, defect data characteristic of primarily only the one or more specified material layers is generated.

Other features and advantages of the invention will appear hereinafter. The features of the invention described above can be used separately or together, or in various combinations of one or more of them. The invention resides as well in sub-combinations of the features described. Furthermore, many of the method steps described herein may be performed in a different order than that which is explicitly described.

BRIEF DESCRIPTION OF THE DRAWINGS

In the drawings, wherein the same reference number indicates the same element in each of the figures.

DETAILED DESCRIPTION OF THE DRAWINGS

Various embodiments of the invention will now be described. The following description provides specific details for a thorough understanding of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Any terminology intended to be interpreted in any restricted manner will be overtly and specifically defined as such in this detailed description section.

Figure 1:
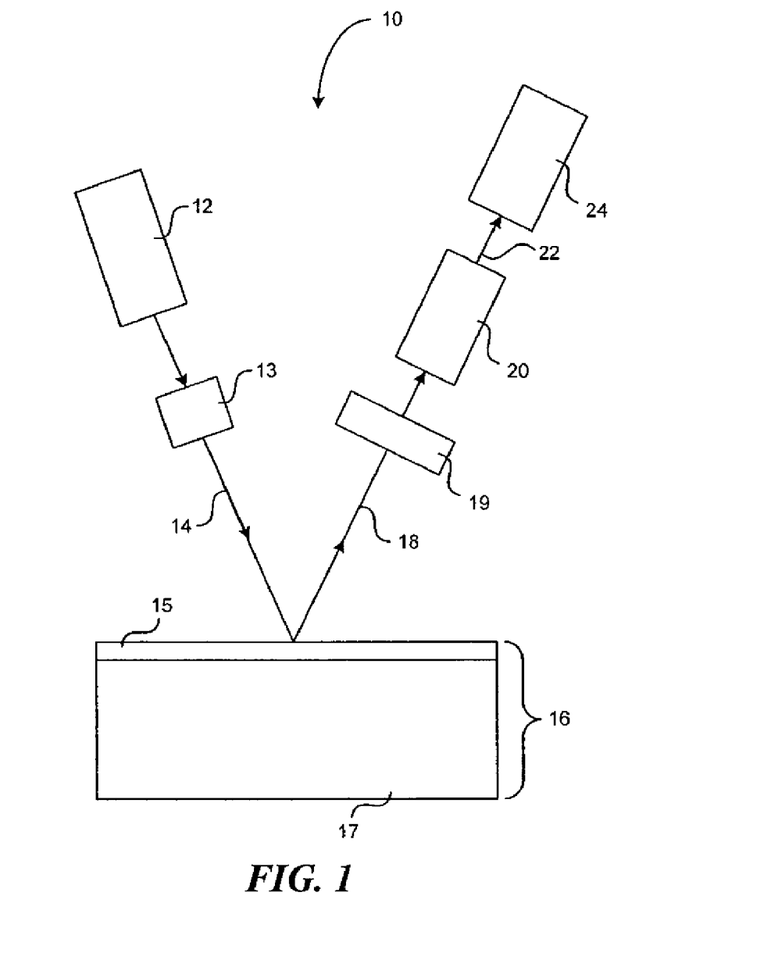
FIG. 1 is a schematic diagram illustrating the basic components of a photoluminescence imaging system, according to a first embodiment.

FIG. 1 schematically illustrates the basic components of a photoluminescence spectroscopy or imaging system 10, according to one embodiment. The photoluminescence imaging system 10 includes a light source 12, such as a laser diode or other suitable light-emitting diode (LED) or device. The light source 12 generates an illumination or incident laser beam 14 or other light beam (e.g., a UV light beam) toward, either directly or via reflection off of one or more optical components, a wafer 16 or other sample. An illumination optic 13, such as a focusing lens or other optical component(s), may optionally be used to focus and/or direct the incident laser beam 114. The term "wafer," as used herein, includes any sample upon which photoluminescence imaging may be performed. The term "laser beam," as used herein, includes any light beam suitable for exciting one or more material layers in the wafer.

The wafer 16 may be a silicon semiconductor wafer or other microelectronic, micro electro-mechanical, or opto-electronic substrate or other sample. The wafer 16 may include one or more epitaxial layers or other surface layers 15 grown on, applied on, or otherwise located on a substrate region or other bulk region 17 of the wafer 16. For example, the wafer 16 may include a bulk region 17 of silicon (Si) and a surface layer 15 of silicon germanium (SiGe). The wafer 16 may include any number of layers including any number of materials and/or compositions. The various wafer layers having different materials and/or compositions will be referred to herein as "material layers." For example, in the wafer just described, the SiGe region is a first material layer, and the Si region is a second material layer.

The incident laser beam 14 penetrates the wafer 16 to a given depth, which is substantially a function of the wavelength of the incident laser beam 14. At least a portion of the incident laser beam 14 is absorbed by the wafer 16 and is emitted from the wafer 16 as return light 18. The emitted return light 18 includes data identifying defects located in the wafer 16 down to the penetration depth (and slightly beyond, due to diffusion) of the laser beam 14. The term "defects," as used herein, includes any contaminants, flaws, discontinuities, impurities, and/or other imperfections present in a wafer 16.

The varying material layers of the wafer 16 each emit return light at a specific wavelength corresponding to the composition of materials in the layer. For example, a typical silicon layer in a wafer 16, at room temperature, may emit return light at a wavelength of approximately 1.07 microns. A typical layer of SiGe, having a 25% Ge concentration, for example, at room temperature, may emit return light at a wavelength of approximately 1.17 microns. The wavelengths at which specific materials and compositions emit return light are well known, and/or can be readily calculated.

The return light 18 emitted from the wafer 16 is collected by a collector 19, such as an objective lens or other suitable optical component(s). Different wavelengths of collected return light correspond to the varying material layers in the wafer 16. The collected return light enters a filter 20 connected to and/or optically aligned with the collector 19. Depending on which wavelength(s) of return light are intended to be detected and measured in a given application, the filter 20 may be a low-pass, high-pass, band-pass, or other suitable filter.

Using the values from the above example, if only wavelengths of return light emitted by the layer of SiGe are to be measured, then a high-pass filter that allows only wavelengths of light above a specified threshold to pass through the filter may be used. For example, a high-pass filter that allows passage of only wavelengths of light above 1.12 microns could be used to allow return light from the SiGe layer (approximately 1.17 microns) to pass, and to prevent return light from the silicon bulk region (approximately 1.07 microns) from passing.

The filter 20 may optionally be an adjustable or variable filter having multiple filtering elements for allowing a variety of wavelengths of light to pass through the filter 20. For example, the filter 20 may be a rotatable wheel or slidable bar element having multiple filtering elements therein, which allows a user to select which wavelength(s) of light will pass through the filter 20. The multiple filtering elements may include one or more low-pass, high-pass, and/or band-pass filters, or may include any other suitable filtering elements.

The return light that passes through the filter 20, referred to herein as filtered return light 22, is detected by a detector 24, such as a CCD array or other suitable detection system connected to and/or optically aligned with the detector 24. A microprocessor, computer, or other processing system is preferably included in, or is connected to or otherwise associated with, the detector 24 for processing data from the filtered return light 22 detected by the detector 24. Thus, only defect data or intensity values characteristic of the desired material layer (the SiGe layer in the above example) is detected and processed. Accordingly, the defect data obtained via this method of selective detection is not obscured or distorted by defect data from other material layer(s) (the Si layer in the above example) in the wafer 16.

The generated defect data may optionally be converted into a visual image indicating the locations and quantity of defects in the specified material layer of the wafer 16. The visual image may be displayed on a monitor or other suitable display screen and/or may be printed out in hard copy form via a printer or similar device. The selective detection process may optionally be performed on one or more additional material layers in the wafer 16 by adjusting the variable filter, or inserting a new filter, to allow passage of return light emitted from the selected material layer(s) in the wafer 16.

In another embodiment, if defect data corresponding to only the bulk region 17, or to another material layer of the wafer 16, is desired, the selective detection method may be used in combination with a bulk probe and a mathematical subtraction process to generate the desired defect data. Using the sample values from above, for example, after the selective detection method is performed to generate defect data corresponding to the SiGe layer of the wafer, a second laser probe penetrating through all or most of the bulk region 17 may be performed.

The bulk probe may be performed using no filter, or using a filter that allows wavelengths of light emitted from both the surface layer 15 (SiGe) and the bulk region 17 (Si) to pass. A high-pass filter set to allow all wavelengths of light greater than 1.00 micron to pass, for example, may be used to allow passage of return light emitted from the SiGe and Si layers, while preventing passage of light having a wavelength of less than one micron, such as light from the incident laser beam, for example.

The defect data obtained from the selective detection probe (i.e., the surface layer defect data) is then mathematically subtracted from the defect data obtained from the bulk probe (which includes surface layer and bulk region defect data) to yield defect data characteristic of defects located primarily in the bulk region 17 of the wafer 16. Put another way, intensity values or defect data points common to both the selective detection probe and the bulk probe (i.e., intensity values or defect data points corresponding to defects primarily in the surface layer 15 of the wafer 16) are mathematically removed from the bulk probe data to produce new defect data characteristic of defects located primarily in the bulk region 17 of the wafer 16.

This subtraction or removal process may be performed via a software program, or any other suitable program or processor, that compares the data points from the surface probe and the bulk probe and subtracts off or otherwise removes the data points common to both probes. The term "primarily," as used herein, means predominantly or entirely, since the generated defect data may not always correspond exactly to defects in the specified material layer(s), due to calibration issues, measurement errors, layer non-uniformity, and so forth.

By removing the defect data corresponding to the surface layer 15, which is often uneven or otherwise flawed, the new defect data, which corresponds primarily to defects in the bulk region 17 of the wafer 16, is no longer distorted by the previously overlying surface layer defect data. Accordingly, a substantially clearer image of the location and concentration of defects present in the bulk region 17 of the wafer 16 may be produced using the new defect data. A visual image of these bulk region defects may be generated using an image-producing device associated with, or located in, the detector 20 and/or with other system elements. The visual image may be displayed on a monitor or other suitable display screen and/or may be printed out in hard copy form via a printer or similar device.

In another embodiment, the surface layer defect data (obtained using the selective detection process) and the bulk probe defect data are normalized relative to each other, before the subtraction process is performed, to enhance the defect images and to make them more easily mathematically processable. The normalization process may include adjusting the contrast and/or the brightness of one or both of the images produced by the selective detection and bulk probes so that they have the same, or substantially the same, relative intensity. Such a normalization process may be performed by a software program or other suitable program or processor, which may be the same as or different than the program or processor that performs the subtraction process.

The normalization process may alternatively or additionally include plotting data points from the selective detection probe versus data points from the bulk probe and removing any mathematically outlying data points, thus yielding images that are more readily mathematically processable. For example, a software program or other suitable program or processor, which may be the same as or different than the program or processor that performs the subtraction process, may curve-fit lines to their respective data points and then remove any outlying data points located beyond a predetermined tolerance limit or distance from the lines.

By normalizing the surface layer defect data relative to the bulk defect data before performing the subtraction process, a clearer, more precise new data set, corresponding to defect data located primarily in the bulk region 17 of the wafer 16, may be obtained. Any other suitable method(s) for normalizing the bulk probe and surface probe data and/or corresponding images relative to each other may additionally or alternatively be used.

A similar selective detection and mathematical subtraction process may be performed to generate optimized defect data characteristic of any material layer in the wafer 16. For example, a low-pass filter may be used to generate first defect data corresponding primarily to the bulk region 17 of the wafer, after which a bulk probe may be performed to generate second defect data corresponding to both the surface layer 15 and the bulk region 17 of the wafer 16. These two sets of data may optionally be normalized relative to each other, and the first defect data may be subtracted from the second defect data to yield new defect data characteristic of defects located primarily in the surface layer 15 of the wafer 16. A similar selective detection and subtracting process may be performed on any material layer of a multi-layer wafer 16, as well.

In another embodiment, the photoluminescence imaging system 10 may be used to perform a selective excitation process, instead of or in conjunction with performing a selective detection process. In this embodiment, the wavelength of the incident laser beam 14 is selected such that it penetrates the wafer 16 approximately to a desired depth and/or to excite one or more selected material layers in the wafer 16. For example, if only defect data from a surface layer 15 having a thickness of 50 nm is desired, then the wavelength of the incident laser beam 14 may be selected so that it penetrates the wafer to a depth of approximately 50 nm. A variable wavelength laser source 12, or a device including multiple laser sources 12, may be used to produce the desired wavelength(s).

Return light 18 emitted from the wafer 16 will therefore include defect data corresponding only to the region of the wafer 16 having a depth approximately equal to the penetration depth (actually slightly beyond, due to diffusion) of the incident laser beam 14. Thus, in the 50 nm surface layer example, the wavelength of the incident laser beam 14 is selected to penetrate the wafer to approximately 50 nm, such that the emitted return light 18 includes defect data primarily characteristic of the surface layer 15 of the wafer 16. The emitted return light 18 is collected by the collector 19, after which it may optionally be passed through a filter 20 to further limit which wavelength(s) of light are allowed to enter the detector 24, as described above. The microprocessor, computer, or other processing system may then process data in the detected return light.

In another selective excitation embodiment, the wavelength of the incident laser beam 14 may be selected such that it is shorter, or has higher energy, than the energy band gap of the material(s) intended to be excited, but is longer, or has lower energy, than the energy band gap of the material(s) not intended to be excited. The shorter the wavelength of the excitation laser, the higher the energy of the laser. The laser's energy must be high enough to excite at least one of the material layers. Using the sample values above, the wavelength of an incident laser beam may be selected such that it has a high enough energy to excite the SiGe layer (which emits return light at a wavelength of 1.17 microns), but does not have a high enough energy to excite the Si layer (which emits return light at a wavelength of 1.07 microns). Thus, return light emitted from the wafer 16 in this example would include defect data characteristic primarily of only the SiGe layer.

Figure 2:
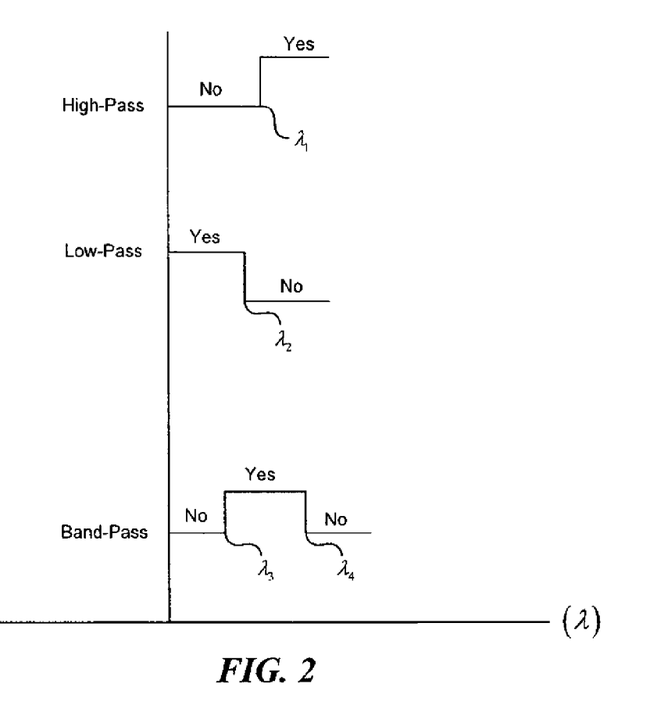
FIG. 2 is a graphical comparison of a high-pass filter, a low-pass filter, and a band-pass filter.

FIG. 2 is a graphical comparison of the operation of a high-pass, a low-pass, and a band-pass filter. A high-pass filter allows wavelengths of light greater than $\lambda_1$ to pass through the filter, while preventing wavelengths of light less than $\lambda_1$ from passing through the filter. A low-pass filter allows wavelengths of light less than $\lambda_2$ to pass through the filter, while preventing wavelengths of light greater than $\lambda_2$ from passing through the filter. A band-pass filter allows wavelengths of light greater than $\lambda_3$ and less than $\lambda_4$ to pass through the filter, while preventing wavelengths of light less than $\lambda_3$ or greater than $\lambda_4$, from passing through the filter. Alternatively, a band-pass filter may prevent wavelengths of light greater than $\lambda_3$ and less than $\lambda_4$ from passing through the filter, while allowing wavelengths of light less than $\lambda_3$, or greater than $\lambda_4$, to pass through the filter.

Figure 3:
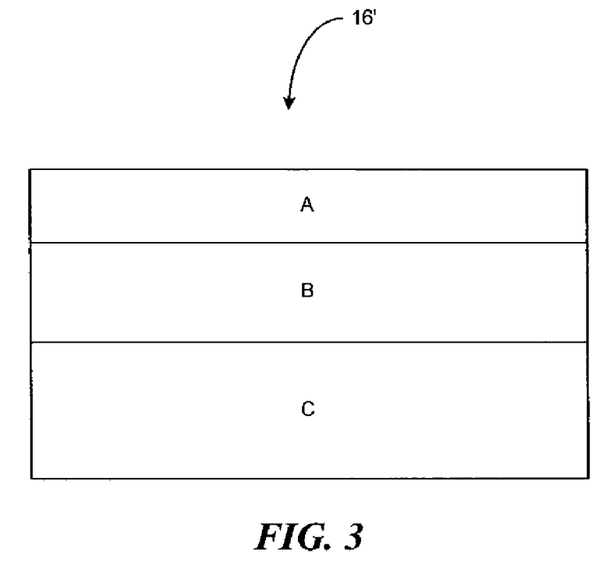
FIG. 3 is a side-view of a multi-layer wafer.

A band-pass filter may be particularly useful when performing photoluminescence imaging on a wafer having more than two layers, such as the three-layer wafer 16' illustrated in FIG. 3. If defect data is desired from only material layer B, for example, and if material layer B emits light at a wavelength $\lambda_B$ that falls between the wavelengths emitted by material layers A ($\lambda_A$) and C ($\lambda_C$), then a band-pass filter that allows the passage of light emitted at wavelengths in a first range encompassing $\lambda_B$, while excluding light emitted at wavelengths above and below the first range, including light emitted at $\lambda_A$ and $\lambda_B$, would yield the desired results.

The photoluminescence imaging systems described herein may include any number of additional or alternative components for performing photoluminescent imaging or spectroscopy on a wafer 16. For example, a photoluminescence imaging system may include a beam splitter for reflecting the incident laser beam 14 toward the wafer 16, and for transmitting the return light 18 toward the collector 19, the filter 20, and/or the detector 20. One or more additional beam splitters or other optical elements or mirrors may be included in the photoluminescence imaging system to achieve a desired size or configuration of the system, and/or to select, focus, collect, and/or direct the incident laser beam 14 and/or the emitted return light 18 throughout the system.

The photoluminescence imaging system may further include an imaging microscope having multiple laser sources, a display screen for visually displaying photoluminescent image data, a printer for printing our hard copies of photoluminescent image data, a wafer holder for supporting the wafer 16, additional filters for filtering incident or return light, and/or any other suitable components. Indeed, a first filter may be used to filter an incident laser beam generated by the light source, while a second filter may be used to filter return light emitted from the wafer 16 (i.e., a combination of selective excitation and selective detection may be used). A detailed example of a photoluminescent imaging system is described in International Application Number PCT/GB97/02388.

The photoluminescence imaging processes described above may be performed at approximately room temperature, also as described in International Application Number PCT/GB97/02388. Alternatively, any of the photoluminescence imaging processes may be performed at higher or lower temperatures, including significantly higher or lower temperatures, depending upon the requirements of a given application.

Any suitable devices and components may be used to perform the photoluminescence processes described herein. For example, various means may be used to produce lasers of varying excitation wavelengths, such as one or more laser diodes or LEDs or other suitable light-producing devices. Any suitable means for collecting emitted return light, such as an objective lens or other optical collector, may be used in the photoluminescence imaging system. Any suitable filtering means, such as a high-pass, low-pass, or band-pass filter may be used to selectively filter emitted return light. Any suitable means for detecting return light may also be used, such as a CCD array, a spectrometer, or any other suitable detecting system or device.

Means for generating defect data based on the detected return light may include a software program or other program or processor, which may be included in or associated with the detector and/or with other elements in the photoluminescence imaging system. Such a program or processor may also be a means for performing the optional subtracting and/or normalizing processes described above. Alternatively, one or more separate programs or processors may be used to perform one or more of these processes.

Thus, while several embodiments have been shown and described, various changes and substitutions may of course be made, without departing from the spirit and scope of the invention. Many of the method steps described herein, for example, may be performed in a different order than that which is specifically described. The invention, therefore, should not be limited, except by the following claims and their equivalents.

What is claimed is:

1. A method for using photoluminescence, comprising:
    directing a laser at a sample having a first material layer and a second material layer, with the first material layer emitting a first return light and with the second material layer emitting a second return light, wherein the first return light and second return light together form combined return light;
    filtering the combined return light to pass the first return light and to remove the second return light;
    detecting the passed first return light; and
    generating first defect data characteristic of the first material layer, using the detected first return light.

2. The method of claim 1 wherein filtering comprises allowing only return light having a wavelength within a predetermined range to pass through the filter.

3. The method of claim 1 wherein filtering comprises either:
    (a) allowing only return light having a wavelength greater than a predetermined wavelength to pass through the filter; or
    (b) allowing only return light having a wavelength less than a predetermined wavelength to pass through the filter.

4. The method of claim 1 wherein the sample includes at least a third material layer, and wherein the laser also penetrates the third material layer.

5. The method of claim 4 wherein the filtering further comprises filtering out third return light emitted from the third material layer.

6. The method of claim 4 further comprising detecting the third return light.

7. The method of claim 4 wherein the first material layer is located between the second and third material layers.

8. The method of claim 1 further comprising:
    penetrating the first material layer and the second material layer of the sample with an additional laser;
    detecting additional return light emitted from the first and second material layers to generate second defect data characteristic of defects in the first and second material layers; and
    subtracting the first defect data from the second defect data to produce third defect data characteristic of defects located primarily in the second material layer.

9. The method of claim 8 further comprising normalizing the first and second defect data relative to each other before performing the subtraction.

10. The method of claim 1 wherein the first material layer is one of a surface layer and a bulk layer of the sample.

11. The method of claim 10 wherein the first material layer is a surface layer comprising SiGe, and the second material layer is a bulk region comprising Si.

12. A method for using photoluminescence, comprising:
    directing a laser beam of a selected wavelength toward a sample to penetrate the sample approximately to a desired depth, the sample emitting return light in response to the directed laser beam, the return light including a first return light that is emitted from a first material layer of the sample and a second return light that is emitted from a second material layer of the sample, wherein the desired depth approximately corresponds to the thickness of a first material layer;
    filtering out a second return light portion of the emitted return light from the sample; and
    detecting a non-filtered first return light portion of the emitted return light to identify defects in the sample.

13. The method of claim 12 wherein the desired depth is approximately equal to a thickness of a surface layer of the sample.

14. A method for using photoluminescence, comprising:
    selecting a laser beam having a wavelength capable of exciting a first material layer, while not exciting a second material layer, in a sample;
    directing the laser beam toward the sample; and
    detecting return light emitted from the excited first material layer to identify defects located in the first material layer.

15. The method of claim 14 wherein an energy of the selected laser beam is greater than an energy band gap of the first material layer, and is less than an energy band gap of the second material layer.

16. A photoluminescence imaging apparatus, comprising:
    a light source for generating a light beam toward a sample;
    a filter for filtering return light emitted from the sample, wherein the filter allows one or more wavelengths of return light emitted from at least a first material layer of the sample to pass through the filter, while preventing one or more additional wavelengths of return light emitted from at least a second material layer of the sample from passing through the filter; and a detector for detecting the first return light that passes through the filter.

17. The apparatus of claim 16 further comprising a collector for collecting the first and second return light.

18. The apparatus of claim 17 wherein the filter is positioned between the collector and the detector.

19. A photoluminescence imaging apparatus, comprising:

means for generating a light beam toward a sample;

means for filtering return light emitted from the sample such that first return light emitted from at least a first material layer of the sample is allowed to pass through the filter, while second return light emitted from at least a second material layer of the sample is prevented from passing through the filter; and means for detecting the first return light that passes through the filtering means.

* * * * *